United States Patent

Bugaut et al.

Patent Number: 4,973,757
Date of Patent: Nov. 27, 1990

[54] PROCESS FOR THE PREPARATION OF NITROANILINES

[75] Inventors: Andree Bugaut, Boulogne-Billancourt; Alex Junino, Aulnay-sous-Bois, both of France

[73] Assignee: L'oreal, Paris, France

[21] Appl. No.: 819,636

[22] Filed: Jan. 17, 1986

Related U.S. Application Data

[63] Continuation of Ser. No. 410,981, Aug. 24, 1982, abandoned.

[30] Foreign Application Priority Data

Aug. 26, 1981 [FR] France .................. 81 16316
Nov. 30, 1981 [FR] France .................. 81 22424

[51] Int. Cl.$^5$ ............... C07C 211/00; C07C 209/00
[52] U.S. Cl. ..................... 564/369; 564/346; 564/367; 564/413; 564/441
[58] Field of Search ............. 564/413, 441, 443, 403, 564/302

[56] References Cited

U.S. PATENT DOCUMENTS

| | | | |
|---|---|---|---|
| 2,448,767 | 9/1948 | Carlson | 564/413 X |
| 2,750,326 | 6/1956 | Eckardt | 564/441 X |
| 3,214,472 | 10/1965 | Charle et al. | 564/403 |
| 4,337,061 | 6/1982 | Bugaut et al. | 564/441 X |
| 4,420,637 | 12/1983 | Bugaut et al. | 564/443 |

FOREIGN PATENT DOCUMENTS

M7975 6/1970 France .
2045991 3/1971 France .

OTHER PUBLICATIONS

Elderfield, "Heterocyclic Compounds", vol. 5, pp. 16–19; 31–36 (1957).
Chemical Substance Index, Ip–Po, vol. 92, Jan.–Jun. 1980, p. 4154 CS.
Corbett, J. F., "A Relationship between Colour and Structure for Simple Nitro Dyes", *J. Soc. Dyers Colour*, vol. 83, No. 7, 1967, p. 275, Tableau 3.
Kobayashi, S. et al., "Cleavage of the Methylenedioxy Ring. II. Cleavage with Sodium Phenoxide and Methoxide in Dimethyl Sulfoxide", *Chem. Pharm. Bull.*, vol. 28, No. 4, 1980, pp. 1287–1288, Tableau 1, formulas, pp. 1289–1293 (1980).
Chemical Abstracts, vol. 92, No. 19, May 12, 1980, p. 596, Ref. No. 163895j.

*Primary Examiner*—Robert V. Hines
*Attorney, Agent, or Firm*—Fleit, Jacobson, Cohn, Price, Holman & Stern

[57] ABSTRACT

The invention relates to a process for the preparation of nitroanilines, which consists in reacting an amine $RNH_2$, or ammonia, with 3,4-methylenedioxynitriobenzene to give the products of the formula:

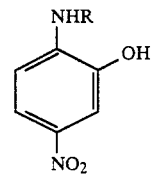

in which R denotes hydrogen, alkyl, monohydroxyalkyl or polyhydroxyalkyl, alkoxyalkyl or aminoalkyl of the formula:

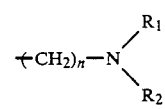

in which $R_1$ and $R_2$, which are identical or different, denote hydrogen, alkyl or monohydroxyalkyl or polyhydroxyalkyl and n denotes an integer from 2 to 4, or of the formula:

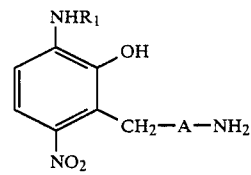

in which A denotes $OCH_2$ or

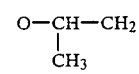

and $R_1$ denotes —$CH_2CH_2OH$ or

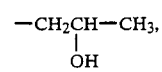

or their salts.

The invention also relates to the dyeing compositions for keratin fibres, and in particular for hair, which contain a dyestuff of the above formula (I) in which R denotes alkyl, polyhydroxyalkyl, alkoxyalkyl or aminoalkyl of the abovementioned formula, and to the dyestuffs of the formula (I) in which R denotes alkoxyalkyl or aminoalkyl of the above formula, and of the formula (IIB), which are novel.

8 Claims, No Drawings

PROCESS FOR THE PREPARATION OF NITROANILINES

This is a continuation of application Ser. No. 410,981 filed Aug. 24, 1982, now abandoned.

The present invention relates to a new process for the preparation of nitroanilines, to the use of these nitroanilines in dyeing compositions for keratin fibres, and in particular for human hair, and to the new nitroanilines prepared by this process.

The present invention relates more particularly to a process for the preparation of compounds of the general formula:

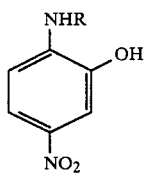
(I)

in which R denotes hydrogen, alkyl, alkyl substituted by one or more OH groups, alkoxyalkyl, or aminoalkyl of the formula:

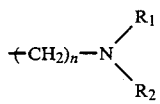

in which $R_1$ and $R_2$ can be identical or different and denote hydrogen, alkyl or alkyl substituted by one or more OH groups, and their salts A certain number of processes are already known which make it possible to prepare compounds belonging to this family of nitroanilines, for example the process described by Bower and Stephens, JCS, 1951, page 325, or in British Patent No. 1 168 105. These processes consist in starting from benzoxazolone and generally comprise three steps. Furthermore, a process is described in British Patent No. 1 012 793 which makes it possible to prepare 2-N-(β-hydroxyethyl)-amino-5-nitrophenol, in particular, by reacting glycol chlorohydrin with 2-amino-5-nitrophenol in the presence of anhydrous sodium acetate and iodine. However, this process has the disadvantage of giving a relatively low yield and of giving rise to the formation of a mixture of compounds which must be separated.

The process according to the invention makes it possible to prepare the compounds of the formula (I) with an improved yield by reacting an amine $RNH_2$, in which R has the meaning indicated above, with 3,4-methylenedioxynitrobenzene. This process is particularly valuable by virtue of the ease with which it can be carried out, since it involves only one step, and by virtue of the purity of the products which can thereby be obtained.

This process also makes it possible to prepare new compounds belonging to the family of the compounds of the formula (I), which are very valuable from the point of view of their use in hair dyeing. In fact, these compounds have the advantage of being very luminous direct dyestuffs having a good resistance to adverse weather conditions and washing, and also a good degree of harmlessness.

The process according to the present invention, which makes it possible to prepare compounds corresponding to the formula:

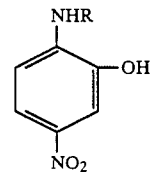

in which R denotes hydrogen, alkyl, monohydroxyalkyl or polyhydroxyalkyl, alkoxyalkyl, or aminoalkyl of the formula:

in which $R_1$ and $R_2$, which are identical or different, denote hydrogen, alkyl or monohydroxyalkyl or polyhydroxyalkyl and n denotes an integer from 2 to 4, and their salts, is characterised in that an amine of the formula $RNH_2$, in which R has the meaning indicated above, or ammonia, is reacted with 3,4-methylenedioxynitrobenzene.

This process can essentially be summarised by the following equation:

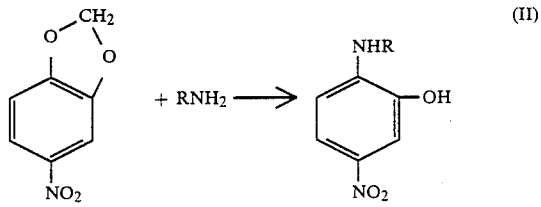
(II)

According to this process, 3,4-methylenedioxynitrobenzene is desirably heated in an excess of amine of the formula $RNH_2$. The operating conditions, such as temperature and reaction time, vary according to the nature of the amine used. The temperature is preferably from 70° to 170° C. and the reaction time is suitably 1 hour to 30 hours.

Once the reaction has ended, the excess amine $RNH_2$ can be removed in vacuo. A virtually pure product can be obtained by carrying out the following processes:

(a) In the case where R is an alkyl, monohydroxyalkyl or polyhydroxyalkyl or alkoxyalkyl group, the crude reaction product, which may or may not still contain the amine $RNH_2$, is treated with a dilute solution of hydrochloric acid. The product insoluble in the dilute hydrochloric acid medium is isolated, washed with water and then treated with a dilute solution of sodium hydroxide. The fraction insoluble in the sodium hydroxide medium, which consists of the unreacted initial product, is removed by filtration. By acidification of the filtrate, the expected product can be obtained virtually pure.

(b) In the case where R denotes the group

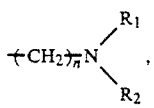

the crude reaction product, which may or may not still contain the amine RNH$_2$, is taken up in a 2 to 3N solution of hydrochloric acid. After cooling, the expected product crystallises in the form of the monohydrochloride. By washing this hydrochloride with a solvent, traces of initial nitro derivative can be removed, if necessary. The hydrochloride can be recrystallised from water.

In the case where R denotes hydrogen, 3,4-methylenedioxynitrobenzene is desirably heated, in an autoclave, in a mixture of ammonia and a non-alcoholic solvent, such as an alkylene glycol ether. After precipitation of the unreacted initial product, filtration and neutralisation with hydrochloric acid, the acetyl derivative can be obtained, which, after acid hydrolysis and neutralisation of the reaction medium, leads to the desired product.

The compounds more particularly prepared according to the invention are those in which R denotes an unsubstituted or hydroxy, alkoxy or amino-substituted alkyl group having 1 to 4 carbon atoms. Amongst these groups, there may be mentioned methyl, ethyl, propyl, n-butyl, β-hydroxyethyl, β-aminoethyl, diethylaminoethyl or β,α-dihydroxypropyl group. The salts are preferably in the form of the hydrochloride, hydrobromide or sulphate.

We have also discovered that, by using, as the amine, an amine of the formula R$_1$NH$_2$, in which R$_1$ denotes CH$_2$CH$_2$—OH or CH$_2$CHOHCH$_3$, the reaction with 3,4-methylenedioxynitrobenzene leads to the formation of two compounds corresponding to the formulae:

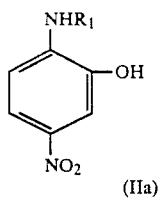 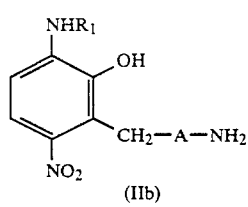

in which R$_1$ has the meaning indicated above and A denotes a group —O—CH$_2$CH$_2$— or

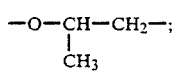

this discovery constitutes a further aspect of the present invention.

This process is essentially characterised in that an amine of the formula R$_1$NH$_2$, in which R$_1$ denotes a group —CH$_2$CH$_2$OH or —CH$_2$CHOHCH$_3$, is reacted with 3,4-methylenedioxynitrobenzene by heating 3,4-methylenedioxynitrobenzene in an excess of amine of the formula R$_1$NH$_2$, at a temperature of, say, 70° to 170° C., for, say, 1 to 30 hours, in that a dilute solution of hydrochloric acid is added to the crude reaction product obtained, in that the product insoluble in the hydrochloric acid medium is filtered off, in that it is purified to give a compound of the formula:

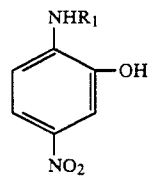

in that the mother liquors from filtration are rendered alkaline with a solution of sodium hydroxide, in that the product which precipitates in the sodium hydroxide medium is isolated and purified, the said product corresponding to the formula:

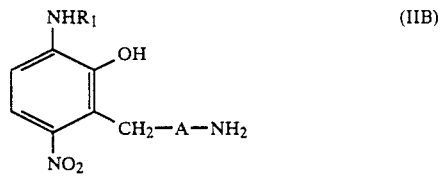

In the process described above, the product insoluble in the dilute hydrochloric acid medium can be separated off and washed and then treated with a dilute solution of sodium hydroxide. The fraction insoluble in the sodium hydroxide medium, which consists of the unreacted initial product, can then be removed by filtration. By acidification of the filtrate, the product of the formula (IIA) can be obtained virtually pure.

The product precipitated from the mother liquors arising from filtration, which have been rendered alkaline, can be obtained after the mother liquors have first been cooled to 0° C. The precipitate is filtered off, washed with water and dried.

The preferred new compounds prepared according to this process correspond to the following formulae:

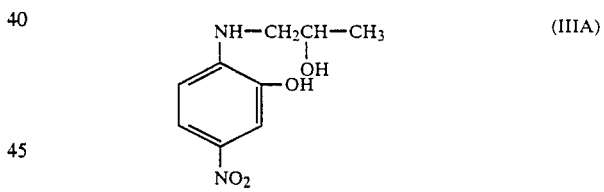

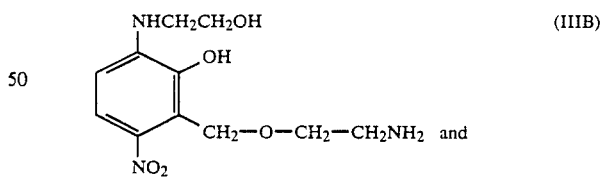

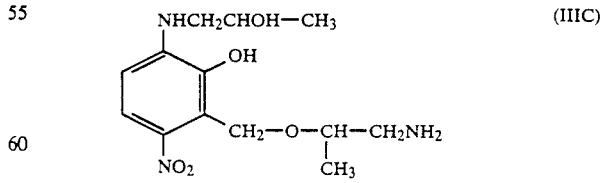

These compounds can also be prepared in the form of their salts, such as the hydrochloride, hydrobromide or sulphate.

The compounds prepared according to the invention are particularly suitable for use in dyeing compositions for keratin fibres, in particular for human hair.

The dyeing compositions for keratin fibres, and in particular for human hair, according to the present invention are essentially characterised in that they contain at least one dyestuff corresponding to the formula:

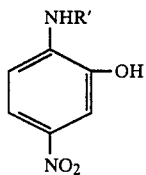 (III)

in which R' denotes an alkyl group, a group

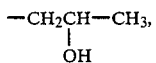

a polyhydroxyalkyl group, an alkoxyalkyl group or an aminoalkyl group of the formula:

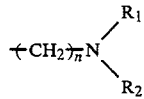

in which $R_1$ and $R_2$, which are identical or different, denote hydrogen, alkyl or monohydroxyalkyl or polyhydroxyalkyl and n is an integer from 2 to 4, or of the formula:

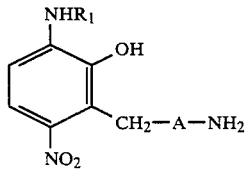 (IIB)

in which $R_1$ denotes the group —CH$_2$CH$_2$OH or —CH$_2$—CHOH—CH$_3$ and A denotes the group —OCH$_2$CH$_2$— or

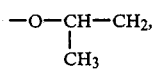

or mixtures thereof, or a cosmetically acceptable salt of these compounds.

These compositions according to the invention, which contain at least one compound corresponding to the formula (III) or (IIB), in a cosmetically acceptable solvent medium, can be used for the direct dyeing of keratin fibres or in the oxidation dyeing of these fibres, in which case the compounds of the formula (III) or (IIB) impart a complementary sheen to the base coloration obtained by oxidative development of oxidation dyestuff precursors.

These compositions suitably contain the compound of formula (III) or (IIB) in an amount from 0.001 to 5% by weight, and preferably 0.01 to 3% by weight, relative to the total weight of the dyeing composition.

They can contain anionic, cationic, non-ionic or amphoteric surface-active agents or mixtures thereof, and preferably cationic and/or non-ionic surface-active agents. These surface-active products are suitably present in the compositions of the invention in an amount from 0.5 to 55% by weight, and preferably 2 to 40% by weight, relative to the total weight of the composition.

In cosmetic application, the cosmetic vehicle generally consists of water; organic solvents can also be included in the compositions in order to solubilise compounds which would not be sufficiently soluble in water. Amongst these solvents, there may be mentioned lower alkanols (i.e. of 1 to 6, especially 1 to 4, carbon atoms), such as ethanol and isopropanol, polyols, such as glycerol, glycols or glycol ethers, such as 2-butoxyethanol, ethylene glycol, ethylene glycol monoethyl ether, propylene glycol, and diethylene glycol monoethyl ether and monomethyl ether, and mixtures thereof. These solvents are preferably present in amounts from 1 to 75% by weight, and in particular from 5 to 50% by weight, relative to the total weight of the composition.

The compositions can be thickened, preferably with sodium alginate, gum arabic, cellulose derivatives, such as methylcellulose, hydroxyethylcellulose, hydroxypropylmethylcellulose and carboxymethylcellulose, and various polymers acting as thickeners, more particularly acrylic acid derivatives It is also possible to use inorganic thickeners, such as bentonite. These thickeners are preferably present in amounts of 0.5 to 10% by weight, and in particular 0.5 to 3% by weight, relative to the total weight of the composition.

The compositions according to the invention can also contain various adjuvants normally used in hair-dyeing sequestering agents, film-forming agents, buffers, perfumes, alkalising agents and acidifying agents.

These compositions can be presented in various forms, such as a liquid, cream or gel or any other form suitable for hair dyeing. Further, they can be packaged in aerosol cans in the presence of a propellant.

The pH of these dyeing compositions is suitably 3 to 11.5 and preferably 5 to 10.5. It is adjusted to the desired value with an alkalising agent, such as ammonia, sodium carbonate, potassium carbonate or ammonium carbonate, sodium hydroxide or potassium hydroxide, alkanolamines, such as mono-, di- or tri-ethanolamine, 2-amino-2-methylpropanol or 2-amino-2-methylpropane-1,3-diol, or alkylamines, such as ethylamine, diethylamine or triethylamine, or with an acidifying agent, such as phosphoric, hydrochloric, tartaric, acetic, lactic or citric acid.

If the compositions are intended for use in a process of direct dyeing of the hair, they can contain, in addition to the compounds according to the invention, other direct dyestuffs, such as azo dyestuffs, anthraquinone dyestuffs, for example tetraminoanthraquinone, aminoquinones, nitrobenzene dyestuffs other than those of formula (III) or (IIB), and, more particularly, the following compounds: 2-methyl-6-nitroaniline, 3-nitro-4-aminophenol, 3-nitro-4-N-($\beta$-hydroxyethyl)-aminophenol, 3-nitro-4-amino-6-methylphenol, 3-amino-4-nitrophenol, 2-amino-3-nitrophenol, 2-amino-5-nitrophenol, 2-($\beta$-hydroxyethyl)-amino-5-nitrophenol, 3-nitro-6-N-($\beta$-hydroxythyl)-aminoanisole, 3-N-($\beta$,$\gamma$-dihydroxypropyl)-amino-4-nitroanisole, 3-N-methylamino-4-nitrophenoxyethanol, 3-N-methylamino-4-nitrophenyl-$\beta$,$\gamma$-dihydroxypropyl ether, N,N'-di-($\beta$-hydroxyethyl)-nitro-paraphenylenediamine and 3-nitro-4-N'-methylamino-N,N-(di-$\beta$-hydroxyethyl)-aniline. The concentration of these direct dyestuffs other than the dyestuffs of the formula (III) or (IIB) is suitably 0.001 to 5% by weight, relative to the total weight of the composition.

These compositions are applied to the keratin fibres for, say, 5 to 70 minutes and the fibres are then rinsed, optionally washed and rinsed again, and dried.

The compositions can be also be used in the form of hair-setting lotions intended both for imparting a slight coloration to the hair and for improving its hold. In this case, they are generally presented in the form of aqueous, alcoholic or aqueous-alcoholic solutions containing at least one cosmetic resin, and they are applied to wet hair which has been washed and rinsed beforehand, which is optionally wound onto rollers and then dried.

The cosmetic resins used in the setting lotions can be, in particular, polyvinylpyrrolidone, crotonic acid/vinyl acetate and vinylpyrrolidone/vinyl acetate copolymers, monoesters of maleic anhydride/butyl vinyl ether and maleic anhydride/methyl vinyl ether copolymers, as well as other cationic, anionic, non-ionic or amphoteric polymers normally used in this type of composition. These cosmetic resins are generally present in the compositions of the invention in amounts of 1 to 3% by weight, and preferably of 1 to 2% by weight, based on the total weight of the composition.

If the compositions constitute oxidation dye formulations, the compounds of the formula (III) or (IIB) are used essentially in order to impart a sheen to the final dyeing.

These compositions then contain oxidation dyestuff precursors in association with at least one nitro dyestuff of the formula (III) or (IIB).

They can contain, for example, para-phenylenediamines, such as: para-phenylenediamine, para-toluylenediamine, 2,6-dimethyl-para-phenylenediamine, 2,6-dimethyl-3-methoxypara-phenylenediamine, N-(β-methoxyethyl)-para-phenylenediamine, 4-N,N-di-(β-hydroxyethyl)-aminoaniline, 4-(N-ethyl-N-carbamylmethyl)-aminoaniline and also their salts.

They can also contain para-aminophenols, such as: para-aminophenol, N-methyl-para-aminophenol, 2-chloro-4-aminophenol, 3-chloro-4-aminophenol, 2-methyl-4-aminophenol and their salts.

They can also contain heterocyclic derivatives, for example: 2,5-diaminopyridine and 7-aminobenzomorpholine.

The compositions according to the invention can contain couplers which are well known in the state of the art, in association with oxidation dyestuff precursors.

Couplers which may be mentioned in particular are: meta-diphenols, such as resorcinol and 2-methylresorcinol, meta-aminophenols such as: meta-aminophenol, 2-methyl-5-aminophenol, 2-methyl-5-N-(β-hydroxyethyl)-aminophenol and 6-hydroxybenzomorpholine and their salts, ethanol, 2,4-diaminophenyl β-hydroxypropyl ether, 6-aminobenzomorpholine, 2-N-(β-hydroxyethyl)-amino-4-aminophenoxyethanol, 2,4-diaminophenyl β,γ-dihydroxypropyl ether and their salts, and meta-acylaminophenols, metaureidophenols and meta-carbalkoxyaminophenols, such as: 2-methyl-5-acetylaminophenol, 2-methyl-5-ureidophenol and 2-methyl-5-carbethoxyaminophenol.

Finally, the following may be mentioned as other couplers which can be used in the compositions of the invention: α-naphthol, couplers possessing an active methylene group, such as diketone compounds and pyrazolones, and heterocyclic couplers such as 2,4-diamino-pyridine, and also their salts.

In addition to the oxidation dyestuff precursors, these compositions may contain reducing agents, such as sodium sulphite, thioglycolic acid, thiolactic acid, sodium bisulphite, ascorbic acid and hydroquinone. These reducing agents are suitably present in amounts of 0.05 to 1.5% by weight, relative to the total weight of the composition. The oxidation dyestuff precursors are suitably present in the compositions of the invention at concentrations of 0.001 to 5% by weight, and preferably 0.03 to 2% by weight, based on the total weight of the composition. The couplers are also suitably present in amounts of 0.001 to 5% by weight and preferably 0.015 to 2% by weight. Their pH is preferably 7 to 11.5 and can be adjusted thereto with the alkalising agents mentioned above.

The process for dyeing keratin fibres, in particular human hair, involving development with an oxidising agent consists in applying, to the hair, the dyeing composition comprising both a dyestuff according to the invention and dyestuff precursor, and in developing the coloration with an oxidising agent, which is either present in the dyeing composition or is applied to the hair in a second step.

The oxidising agent is preferably hydrogen peroxide, urea peroxide or a per-salt. A solution of hydrogen peroxide of 20 volumes strength can be used in particular.

Once the composition has been applied to the keratin fibres with the oxidising agent, a period of 10 to 50 minutes, preferably 15 to 30 minutes, is generally allowed, after which the keratin fibres are rinsed, optionally shampooed and rinsed again, and dried.

Of these compositions, the ones which are particularly preferred are those which contain nitro dyestuffs of the formula (III) in which R' denotes alkoxyalkyl or a group of the formula:

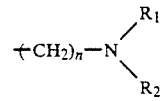

in which $R_1$ and $R_2$ and n have the meanings indicated above.

These compounds are new compounds and give rise to very luminous yellow colorations which, when the compounds are used in compositions described above, have a good resistance to adverse weather conditions and washing and also a good degree of harmlessness.

The following Examples further illustrate the present invention.

PREPARATION EXAMPLE 1

Preparation of 2-N-butylamino-5-nitrophenol

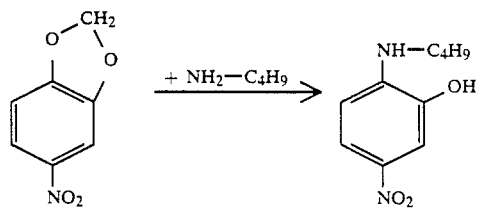

100 g (0.6 mol) of 3,4-methylenedioxynitrobenzene in 400 ml of butylamine are heated under reflux for 26 hours. The major part of the butylamine is removed by distillation in vacuo and the residual product is treated with one litre of a 0.5N solution of hydrochloric acid. This gives a very thick gum which, after first being washed with a 0.5N solution of hydrochloric acid and then with water, is treated with one liter of a normal solution of sodium hydroxide, with stirring. The insoluble fraction, which consists of the unreacted 3,4-methylenedioxynitrobenzene, is filtered off. The filtrate containing sodium hydroxide is washed twice in succession by extraction with 300 ml of chloroform and then, after cooling to 0° C., it is neutralised by adding hydrochloric acid of density 1.18. The expected product precipitates. It is filtered off, washed with water and then dried in vacuo.

This gives 45 g of virtually pure 2-N-butylamino-4-nitrophenol monohydrate, which melts at 64° C.

After two recrystallisations from benzene and drying in vacuo at 80° C. for 8 hours, the product melts at 95° C. This is anhydrous 2-N-butylamino-5-nitrophenol.

| Analysis | Calculated for $C_{10}H_{14}N_2O_3$ | Found |
|---|---|---|
| C % | 57.14 | 57.23 |
| H % | 6.67 | 6.73 |
| N % | 13.38 | 13.42 |
| O % | 22.86 | 22.66 |

PREPARATION EXAMPLE 2

Preparation of 2-N-(β-hydroxyethyl)-amino-5-nitrophenol

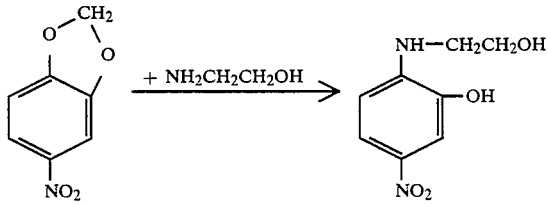

0.299 mol (50 g) of 3,4-methylenedioxynitrobenzene in 250 ml of monoethanolamine are heated in a boiling water-bath for 3½ hours, with stirring. After the reaction medium has cooled, it is poured into 2 liters of iced water to which 300 ml of hydrochloric acid of density 1.18 have been added. The expected product precipitates. It is filtered off, washed with water and then dissolved in 300 ml of a normal solution of sodium hydroxide. By filtration of this sodium hydroxide solution, a few grams of initial product are removed. The filtrate is acidified to pH 2 with a 5N solution of hydrochloric acid in order to precipitate the 2-N-(β-hydoxyethyl)-amino-5-nitrophenol. The product is filtered off, washed with water and dried in vacuo. This gives 35 g of virtually pure product (melting point=207° C.). After recrystallisation from ethanol, the product melts at 208° C.

| Analysis | Calculated for $C_8H_{10}N_2O_4$ | Found |
|---|---|---|
| C % | 48.48 | 48.39 |
| H % | 5.09 | 5.27 |
| N % | 14.14 | 14.32 |

PREPARATION EXAMPLE 3

Preparation of 2-N-(β-diethylaminoethyl)-amino-5-nitrophenol

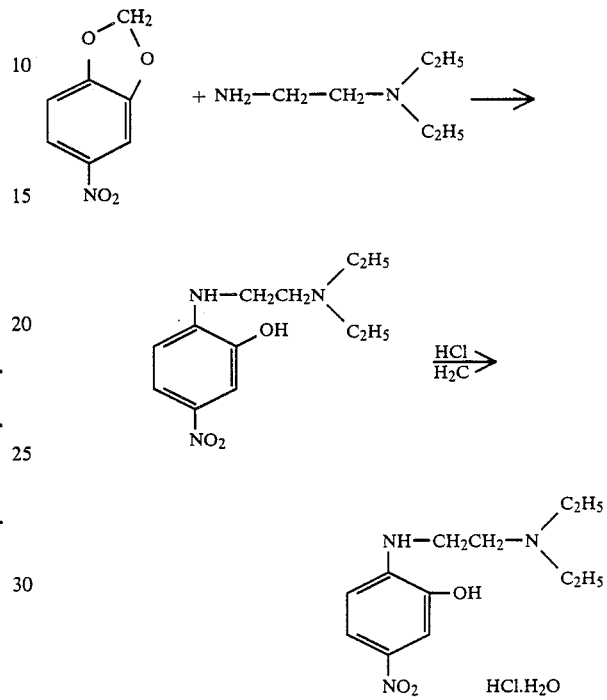

0.718 mol (120 g) of 3,4-methylenedioxynitrobenzene in 480 ml of N,N-diethylethylenediamine are heated for 15 hours in a boiling water-bath, with stirring. After the reaction mixture has cooled, it is poured into 4,480 ml of iced water to which 1,330 ml of hydrochloric acid of density 1.18 have been added. The expected product crystallises and is filtered off, washed carefully with a 2N solution of hydrochloric acid and then dried in vacuo.

This gives 135 g of virtually pure 2-N-(β-diethylaminoethyl)-amino-5-nitrophenol monohydrochloride monohydrate.

After two recrystallisations from water (7 ml per gram), the product is dried in vacuo.

It melts with decomposition at 221° C.

| Analysis | Calculated for $C_{12}H_{22}N_3O_4Cl$ | Found |
|---|---|---|
| C % | 46.83 | 46.48 |
| H % | 7.15 | 7.27 |
| N % | 13.66 | 13.66 |
| O % | 20.81 | 21.07 |
| Cl % | 11.55 | 11.46 |

PREPARATION EXAMPLE 4

Preparation of 2-N-(β-aminoethyl)-amino-5-nitrophenol monohydrochloride monohydrate

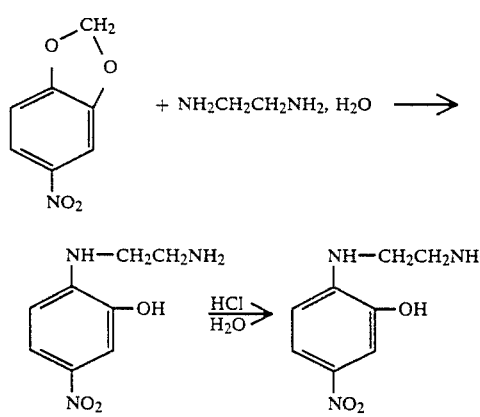

0.179 mol (30 g) of 3,4-methylenedioxynitrobenzene in 150 ml of ethylenediamine are heated in a boiling water-bath for one hour, with stirring. After the reaction medium has cooled, it is poured into 1,400 ml of iced water to which 590 ml of hydrochloric acid of density 1.18 have been added. The orange solution is kept at $-10°$ C. for two days. The 2-N-(β-aminoethyl)-amino-5-nitrophenol monohydrochloride monohydrate which has crystallised is filtered off and then washed with a 2N solution of hydrochloric acid and then with iced water. It is dried in vacuo.

This gives 20 g of virtually pure product. melting point (with decomposition)=253° C.

The product is recrystallised from water and then dried.

| Analysis | Calculated for $C_8H_{14}N_3O_4Cl$ | Found |
| --- | --- | --- |
| C % | 38.17 | 38.16 |
| H % | 5.56 | 5.43 |
| N % | 16.70 | 16.94 |
| O % | 25.45 | 25.36 |
| Cl % | 14.11 | 14.27 |

PREPARATION EXAMPLE 5

Preparation of 2-amino-5-nitrophenol.

A solution of 0.18 mol (30 g) of 3,4-methylenedioxynitrobenzene in a mixture of 240 ml of 28% strength ammonia solution and 240 ml of diethylene glycol dimethyl ether is heated at 100° C. for 28 hours in an autoclave. After cooling, 480 ml of water are added. The unreacted initial product precipitates. It is recovered by filtration and the filtrate is then neutralised with hydrochloric acid. After filtration, the filtrate is extracted with ethyl acetate. The ethyl acetate is driven off in vacuo. The residue is treated with 25 ml of acetic anhydride and then kept in a boiling water-bath for 30 minutes. After cooling, the expected product is isolated in the form of the acetyl derivative. This acetyl derivative is hydrolysed with 45 ml of hydrochloric acid of density 1.17, at 90° C. for one hour. After dilution and neutralisation of the solution containing hydrochloric acid, 2-amino-5-nitrophenol is isolated by filtration. Melting point=207° C.

PREPARATION EXAMPLE 6

Preparation of 2-[2-hydroxy-3-N-(β-hydroxyethyl)-amino-6-nitrobenzyloxy]-ethylamine.

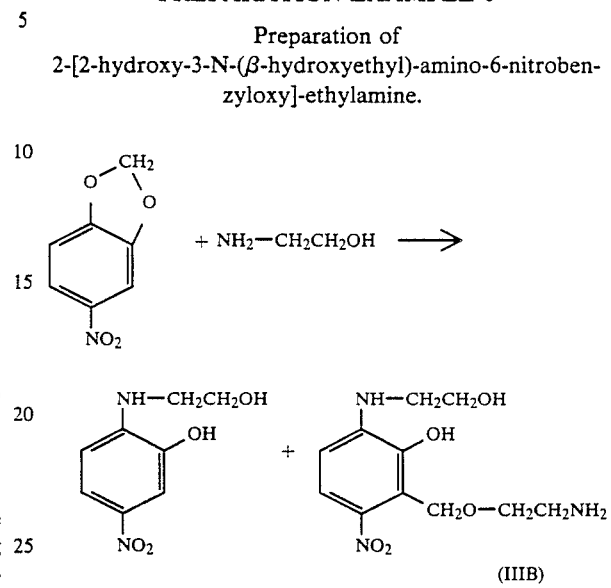

The preparation of 2-N-(β-hydroxyethyl)-amino-5-nitrophenol has already been described in Example 2 above. During this preparation, after heating 0.299 mol (50 g) of 3,4-methylenedioxynitrobenzene in 250 ml of monoethanolamine for 3½ hours, the reaction medium is poured into 2 liters of iced water to which 300 ml of hydrochloric acid of density 1.18 have been added. The 2-N-(β-hydroxyethyl)-amino-5-nitrophenol is filtered off and is purified by the process described. The melting point is 207° C. and the yield 59%.

The mother liquors from filtration, cooled to 0° C., are rendered alkaline to pH 10 with a 5N solution of sodium hydroxide.

2-[2-Hydroxy-3-N-(β-hydroxyethyl)-amino-6-nitrobenzyloxy]-ethylamine precipitates immediately and is filtered off, washed with water and dried. This gives 15 g of chromatographically pure product. The melting point is 190° C.

| Analysis | Calculated for $C_{11}H_{17}N_3O_5$ | Found |
| --- | --- | --- |
| C % | 48.70 | 48.38 |
| H % | 6.32 | 6.35 |
| N % | 15.49 | 15.50 |

PREPARATION EXAMPLE 7

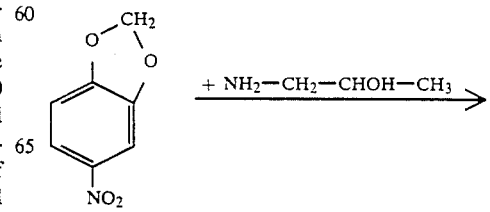

-continued

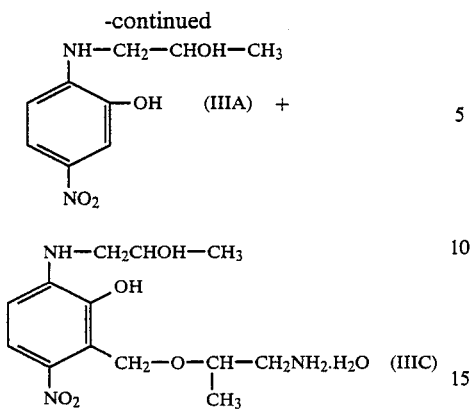

A. Preparation of 2-N-(β-hydroxypropyl)-amino-5-nitrophenol 0.418 mol (70 g) of 3,4-methylenedioxynitrobenzene in 350 ml of 1-aminopropan-2-ol are heated for 8 hours in a boiling-water bath and the cooled reaction medium is then poured into 1,500 ml of iced water. About 5 g of unreacted initial product are removed by filtration.

The filtrate is treated with 330 ml of hydrochloric acid of density 1.18, with stirring, so as to give a pH of 3.5. The expected product precipitates in the form of crystals. It is filtered off, washed with water and recrystallised from alcohol. After drying, 32 g of product are obtained. The melting point is 184° C. Yield: 36.3%.

| Analysis | Calculated for $C_9H_{12}N_2O_4$ | Found |
|---|---|---|
| C % | 50.94 | 50.88 |
| H % | 5.70 | 5.69 |
| N % | 13.20 | 13.26 |

B. Preparation of 2-[2-hydroxy-3-N-(β-hydroxypropyl)-amino-6-nitrobenzyloxy]-propylamine monohydrate.

After the 2-N-(β-hydroxypropyl)-amino-5-nitrophenol phenol has been filtered off, the mother liquors, cooled to 0° C., are rendered alkaline to pH 10 with a 5N solution of sodium hydroxide and then saturated with sodium chloride, with stirring. The expected product precipitates. It is filtered off, washed with water and redissolved in 140 ml of a 0.5N solution of hydrochloric acid for the purpose of purification. After filtration to remove a small amount of insoluble material, this solution containing hydrochloric acid is extracted twice with ethyl acetate in order to remove a small amount of 2-N-(β-hydroxypropyl)-amino-5-nitrophenol. It is then rendered alkaline with ammonia solution. The expected product precipitates. It is filtered off, washed with water and recrystallised twice from alcohol. After drying in vacuo, it melts at 142° C.

| Analysis | Calculated for $C_{13}H_{12}O_5N_3.H_2O$ | Found |
|---|---|---|
| C % | 49.21 | 49.26 |
| H % | 7.25 | 7.22 |
| N % | 13.25 | 13.24 |

PREPARATION EXAMPLE 8

Preparation of 2-N-(β,γ-dihydroxypropyl)amino-5-nitrophenol

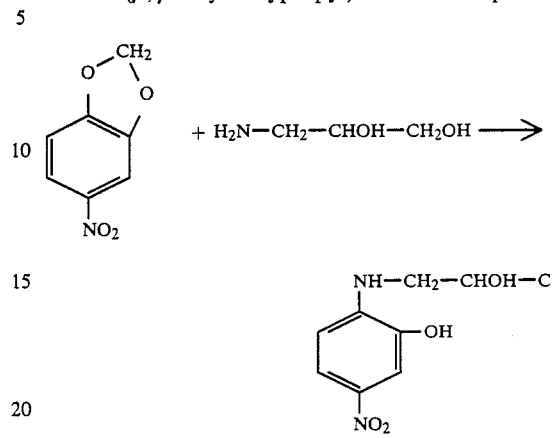

10 g (0.0599 mol) of 3,4-methylenedioxynitrobenzene and 50 g (0.549 mol) of 1-amino-2,3-propanediol in 25 ml of dimethylsulfoxide are heated to about 100° C. for 10½ hours. The reaction mixture is poured into 250 g of iced water. By filtration, 0.4 g of the starting nitro compound are removed. The filtrate is acidified to pH 3 with 25 ml of 35% strength hydrochloric acid and then treated with 100 g of sodium chloride before being extracted with ethyl acetate. The extraction ethyl acetate is driven off in vacuo. The residual oil (12 g) is fractionated by chromatography on silica gel 60 (MERCK). The purified expected product is eluted with a toluene/ethyl acetate (60/40) mixture. The solvent is driven off in vacuo. The expected product crystallises and melts at 97° C. (6.7 g; yield=49%)

EXAMPLE 1

The following dyeing composition is prepared:

| | |
|---|---|
| 2-N-(β-Diethylaminoethyl)-amino-5-nitrophenol monohydrochloride | 0.25 g |
| 3-Nitro-4-N-(β-aminoethyl)-aminophenoxyethanol | 0.26 g |
| 3-Nitro-4-N'-methylamino-N-(β-aminoethyl)-aniline dihydrobromide | 0.38 g |
| 96° strength ethanol | 10 g |
| Cemulsol NP4 | 12 g |
| Cemulsol NP9 | 15 g |
| Oxyethyleneated oleyl alcohol containing 2 mols of ethylene oxide | 1.5 g |
| Oxyethyleneated oleyl alcohol containing 4 mols of ethylene oxide | 1.5 g |
| 20% strength aqueous solution of triethanolamine | 0.5 g |
| Water q.s. | 100 g |
| pH 7.5 | |

When applied for 30 minutes at 28° C. to hair which has been bleached white, this mixture imparts to the hair, after rinsing and shampooing, a copper-red coloration.

EXAMPLE 2

The following dyeing composition is prepared:

| | |
|---|---|
| 2-N-(β-Aminoethyl)-amino-5-nitrophenol monohydrochloride monohydrate | 0.215 g |
| 2-N-(β-Hydroxyethyl)-amino-5-[4-N,N-di(β-hydroxyethyl)-aminoanilino]-1,4-benzoquinone | 0.2 g |

-continued

| | |
|---|---|
| 3-Nitro-4-N-(β-hydroxyethyl)-aminophenol | 0.105 g |
| 3-Nitro-4-(β-hydroxyethyl)-aminophenyl β-hydroxypropyl ether | 0.2 g |
| 2-Butoxyethanol | 10 g |
| Cellosize WP03 | 2 g |
| Dimethyl-alkyl(copra)-hydroxyethylammonium chloride | 2 g |
| 20% strength aqueous solution of monoethanolamine | 0.25 g |
| Water q.s. | 100 g |
| pH 8.5 | |

When applied for 35 minutes at 30° C. to hair which has been bleached straw yellow, this mixture imparts to the hair, after rinsing and shampooing, an intense red coloration.

EXAMPLE 3

The following dyeing composition is prepared:

| | |
|---|---|
| 2-N-Butylamino-5-nitrophenol | 0.205 g |
| 2-Nitro-N-(β-aminoethyl)-aniline hydrochloride | 0.205 g |
| 3-Nitro-4-amino-6-methyl-N-(β-aminoethyl)-aniline monohydrobromide monohydrate | 0.4 g |
| Tetraaminoanthraquinone | 0.31 g |
| Carboxymethylcellulose | 2 g |
| 2-Butoxyethanol | 10 g |
| Ammonium lauryl-sulphate | 5 g |
| 5% strength ammonia solution | 1 g |
| Water q.s. | 100 g |

When applied for 20 minutes at 30° C. to hair which has been bleached white, this mixture imparts to the hair, after rinsing and shampooing, a coppery chestnut coloration.

EXAMPLE 4

The following dyeing composition is prepared:

| | |
|---|---|
| 2-N-Butylamino-5-nitrophenol | 1.5 g |
| 3-Nitro-4-N-(β-hydroxyethyl)-aminophenol | 0.2 g |
| 3-Nitro-4-N'-methylamino-N,N-di-(β-hydroxyethyl)-aniline | 0.51 g |
| 2-Butoxyethanol | 10 g |
| Cemulsol NP4 | 12 g |
| Cemulsol NP9 | 15 g |
| Oxyethyleneated oleyl alcohol containing 2 mols of ethylene oxide | 1.5 g |
| Oxyethyleneated oleyl alcohol containing 4 mols of ethylene oxide | 1.5 g |
| 20% strength aqueous solution of triethanolamine | 0.15 g |
| Water q.s. | 100 g |
| pH 8.5 | |

When applied for 20 minutes at 30° C. to hair which has been bleached white, this mixture imparts to the hair, after rinsing and shampooing, a coppery blond coloration.

EXAMPLE 5

The following dyeing composition is prepared:

| | |
|---|---|
| 2-N-(β-Aminoethyl)-amino-5-nitrophenol monohydrochloride monohydrate | 0.03 g |
| 2-N-(β-Hydroxyethyl)-amino-5-nitrophenol | 0.15 g |
| 3-Nitro-4-amino-6-methyl-N-(β-hydroxyethyl)-aniline | 0.07 g |
| 3-Nitro-4-N'-methylamino-N,N-di-(β-hydroxyethyl)-aniline | 0.15 g |
| 2-Butoxyethanol | 10 g |
| Lauramide | 1.5 g |
| Hydroxyethylcellulose | 5 g |

-continued

| | |
|---|---|
| Lauric acid | 1 g |
| Monoethanolamine | 2 g |
| Water q.s. | 100 g |
| pH 10 | |

When applied for 20 minutes at 30° C. to hair which has been bleached white, this mixture imparts to the hair, after rising and shampooing, a light mahogany coloration.

EXAMPLE 6

The following dyeing composition is prepared:

| | |
|---|---|
| 2-N-(β-Diethylaminoethyl)-amino-5-nitrophenol monohydrochloride | 0.1 g |
| 3-Nitro-4-aminophenol | 0.09 g |
| 3-Nitro-4-N'-methylamino-N,N-di-(β-hydroxyethyl)-aniline | 0.17 g |
| 3-Nitro-4-amino-6-methyl-N-(β-hydroxyethyl)-aniline | 0.05 g |
| 2-Butoxyethanol | 10 g |
| Cellosize WP 03 | 2 g |
| Dimethyl-alkyl(copra)-hydroxyethylammonium chloride | 2 g |
| 20% strength by weight aqueous solution of monoethanolamine | 0.5 g |
| Water q.s. | 100 g |
| pH 8.7 | |

When applied for 30 minutes at 30° C. to hair which has been bleached straw yellow, this mixture imparts to the hair, after rinsing and shampooing, a coppery chestnut coloration.

The examples which follow are intended to illustrate other compositions according to the invention. In these examples, the colorations obtained are expressed by the Munsell notations, after an application time of 30 minutes at 30° C.

EXAMPLE 7

| | |
|---|---|
| 2-N-Butylamino-5-nitrophenol | 0.8 g |
| 96° strength ethanol | 10 g |
| Alfol C$_{16/18}$ | 8 g |
| Lanette wax E | 0.5 g |
| Cemulsol B | 1 g |
| Oleic diethanolamide | 1.5 g |
| 20% strength aqueous solution of triethanolamine | 1 g |
| Water q.s. | 100 g |
| pH = 8 | |
| On bleached hair: 4 Y 8/9 | |
| on 90% naturally white hair: 4.5 Y 6/7. | |

EXAMPLE 8

| | |
|---|---|
| 2-N-(β-Aminoethyl)-amino-5-nitrophenol monohydrochloride monohydrate | 1.2 g |
| 96° strength ethanol | 10 g |
| Hydroxyethylcellulose | 2 g |
| Dimethyl-alkyl(copra)-hydroxyethylammonium chloride | 2 g |
| 20% strength aqueous solution of monoethanolamine | 1 g |
| Water q.s. | 100 g |
| pH 6 | |
| on bleached hair: 3 Y 8/12 | |
| on 90% naturally white hair: 3.5 Y 6.5/8. | |

EXAMPLE 9

| | |
|---|---|
| 2-N-(β-Aminoethyl)-amino-5-nitrophenol monohydrochloride monohydrate | 0.04 g |
| Diethanolamides of copra fatty acids | 2.2 g |
| Lauric acid | 0.8 g |
| 96° strength ethanol | 5 g |
| Ethylene glycol monoethyl ether | 2 g |
| Monoethanolamine | 1 g |
| Water q.s. | 100 g |
| pH 6.7 | |
| On bleached hair: 4.5 Y 8/6 | |

EXAMPLE 10

| | |
|---|---|
| 2-N-(β-Diethylaminoethyl)-amino-5-nitrophenol monohydrochloride | 1.96 g |
| 96° strength ethanol | 10 g |
| Carbopol 934 | 2 g |
| 22° B strength ammonia solution | 3 g |
| Water q.s. | 100 g |
| pH 9 | |
| On bleached hair: 2.5 Y 8/12 | |
| On 90% naturally white hair: 4 y 6/8 | |

EXAMPLE 11

The following dyeing composition is prepared:

| | |
|---|---|
| 2-N-(β-Hydroxypropyl)-amino-5-nitrophenol | 0.6 g |
| 2-Butoxyethanol | 10 g |
| Alfol C$_{16}$/C$_{18}$ | 8 g |
| Lanette wax E | 0.5 g |
| Cemulsol B | 1 g |
| Oleic diethanolamide | 1.5 g |
| 5% strength ammonia solution | 1 g |
| Water q.s. | 100 g |
| pH 8.8 | |

When applied to bleached hair for 30 minutes at 30° C., this mixture imparts to the hair, after rinsing and shampooing, a coloration of 5 Y 7/10 according to the Munsell notation.

EXAMPLE 12

The following dyeing composition is prepared:

| | |
|---|---|
| 2-N-(β-Hydroxypropyl)-amino-5-nitrophenol | 0.2 g |
| Tetraaminoanthraquinone | 0.35 g |
| 3-Nitro-4-N-(β-hydroxyethyl)-aminophenol | 0.1 g |
| 3-Nitro-4-amino-6-methyl-N-(β-hydroxyethyl)- | 0.05 g |
| Propylene glycol | 10 g |
| Cellosize WP 03 | 2 g |
| Cetyldimethylhydroxyethylammonium chloride | 2 g |
| 20% strength solution of triethanolamine | 1 g |
| Water q.s. | 100 g |
| pH 8.2 | |

When applied to bleached hair for 20 minutes at 30° C., this mixture imparts to the hair, after rinsing and shampooing, a coppery blond coloration.

EXAMPLE 13

The following dyeing composition is prepared:

| | |
|---|---|
| 2-[2-Hydroxy-3-N-(β-hydroxypropyl)-amino-6-nitrobenzyloxy]-propylamine | 0.45 g |
| Propylene glycol | 10 g |
| Carbopol 934 | 2 g |
| 5% strength ammonia solution | 3 g |
| Water q.s. | 100 g |
| pH 5.2 | |

When applied to bleached hair for 30 minutes at 30° C., this mixture imparts to the hair, after rinsing and shampooing, a coloration of 1.5 Y 7/10 according to the Munsell notation.

EXAMPLE 14

The following dyeing composition is prepared:

| | |
|---|---|
| 2-[2-Hydroxy-3-N-(β-hydroxypropyl)-amino-6-nitrobenzyloxy]-propylamine | 0.45 g |
| Propylene glycol | 10 g |
| Carbopol 934 | 2 g |
| 20% strength solution of monoethanolamine | 7 g |
| Water q.s. | 100 g |
| pH 7.7. | |

When applied to bleached hair for 20 minutes at 28° C., this mixture imparts to the hair, after rinsing and shampooing, a coloration of 5 YR 6/11 according to the Munsell notation.

EXAMPLE 15

The following dyeing composition is prepared:

| | |
|---|---|
| 2-[2-Hydroxy-3-N-(β-hydroxypropyl)-amino-6-nitrobenzyloxy]-propylamine | 0.15 g |
| 2-N-(β-Hydroxyethyl)-amino-5-[4-N,N-di-(β-hydroxyethyl)-aminoanilino]-1,4-benzoquinone | 0.15 g |
| 3-Nitro-4-amino-N-(β-hydroxyethyl)-aniline | 0.13 g |
| 3-Nitro-4-N'-(β-aminoethyl)-amino-N,N-di-(β-hydroxyethyl)-aniline hydrochloride | 0.03 g |
| 96° strength ethanol | 5 g |
| Diethanolamides of copra fatty acids | 2.2 g |
| Lauric acid | 0.8 g |
| Ethylene glycol monoethyl ether | 2 g |
| 20% strength solution of monoethanolamine | 1 g |
| Water q.s. | 100 g |
| pH 8.4 | |

When applied to bleached hair for 25 minutes at 30° C., this mixture imparts to the hair, after rinsing and shampooing, a copper coloration with a purple sheen.

EXAMPLE 16

The following dyeing composition is prepared:

| | |
|---|---|
| 2-[2-Hydroxy-3-N-(β-hydroxyethyl)-amino-6-nitrobenzyloxy]-ethylamine | 0.54 g |
| 10% strength solution of lactic acid | 0.5 g |
| Carboxymethylcellulose | 2 g |
| Ammonium lauryl-sulphate | 5 g |
| 2-Butoxyethanol | 10 g |
| Water q.s. | 100 g |
| pH 6.2 | |

When applied to bleached hair for 20 minutes at 30° C., this mixture imparts to the hair, after rinsing and shampooing, a coloration of 7.5 YR 6/10 according to the Munsell notation.

EXAMPLE 17

The following dyeing composition is prepared:

| | |
|---|---|
| 2-[2-Hydroxy-3-N-(β-hydroxyethyl)-amino-6-nitrobenzyloxy]-ethylamine | 0.25 g |
| 3-Nitro-4-N'-(β-aminoethyl)-amino-N,N-di-(β-hydroxyethyl)-aniline hydrochloride | 0.095 g |
| 2-Methyl-4-amino-5-nitrophenol | 0.065 g |
| 2-Butoxyethanol | 10 g |
| Water q.s. | 100 g |
| pH 6.25 | |

When applied to 95% naturally white hair for 25 minutes at 28° C., this mixture imparts to the hair, after rinsing and shampooing, a coppery light blond coloration.

The reference examples which follow are intended to illustrate the preparation of the 3-nitro-4-N-(β-aminoethyl)-aminophenoxyethanol used in Example 1 and the preparation of the 3-nitro-4-(β-hydroxyethyl)-aminophenyl β-hydroxypropyl ether used in Example 2.

EXAMPLE 18

The following dyeing composition is prepared:

| | |
|---|---|
| 2-N-(β,γ-dihydroxypropyl)amino-5-nitropenol | 3 g |
| 96° strength ethanol | 10 g |
| Cellosize WP 03 | 2 g |
| 5% strength ammonia solution | 1.5 g |
| Water qs | 100 g |
| pH 8.20 | |

When applied for 20 minutes at 20° C. to hair which has been bleached to white, this mixture impacts to the hair, after rinsing and shampooing, a very intense orange coloration.

EXAMPLE 19

The following dyeing composition is prepared:

| | |
|---|---|
| 2-N-(β,γ-dihydroxypropyl)amino-5-nitriophenol | 0.4 g |
| paraphenylenediamine | 0.265 g |
| paraaminophenol | 0.4 g |
| 2,4-diaminophenoxyethanol dihydrochloride | 0.105 g |
| resorcinol | 0.25 g |
| metaaminophenol | 0.21 g |
| 2-methyl-5-N-(β-hydroxyethyl)aminophenol | 0.15 g |
| Cemulsol NP4 | 21 g |
| Cemulsol NP 9 | 24 g |
| Oleic acid | 4 g |
| 2-butoxyethanol | 3 g |
| 96° strength ethanol | 10 g |
| Masquol DTPA (sodium salt of diethylenetriamine pentaacetic acid) | 2.5 g |
| 35° B strength sodium bisulphite solution | 1 g |
| 22° B strength ammonia solution | 10 g |
| water q.s. | 100 g |
| pH = 10.3 | |

100 g of hydrogen peroxide of 20 volumes strength are added at the time of application.

When applied for 20 minutes at 28° C. to hair which has been bleached to white, this mixture imparts to the hair, after rinsing and shampooing, a golden chestnut coloration.

EXAMPLE 20

The following dyeing composition is prepared:

| | |
|---|---|
| 2-N-(β,γ-dihydroxypropyl)amino-5-nitrophenol | 0.42 g |
| 1-N-(β-aminoethyl)amino-2-nitro-4-N',N'-di(β-hydroxyethyl)aminobenzene | 0.265 g |
| 1-amino-2-nitro-4-N-(β-hydroxyethyl)amino-5-methylbenzene | 0.31 g |
| Carbopol 934 | 2 g |
| Monoethanolamine (20% strength aqueous solution) | 10 g |
| Water qs | 100 g |
| pH: 8 | |

When applied for 25 minutes at 28° C. to 90% naturally white hair, this mixture imparts to the hair, after rinsing and shampooing, a copper coloration.

REFERENCE EXAMPLE 1

Preparation of 3-nitro-4-(β-aminoethyl)-aminophenoxyethanol

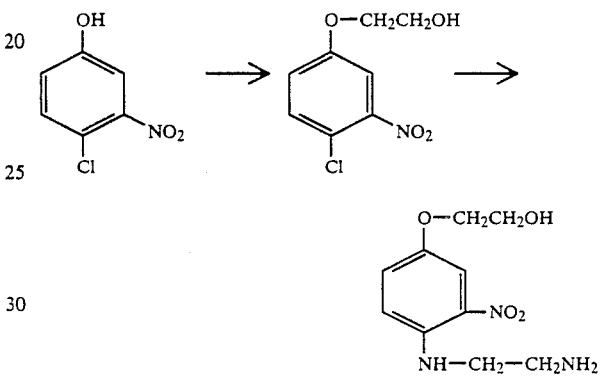

1st step: Preparation of 3-nitro-4-chlorophenoxyethanol.

2.5 mols (434 g) of 4-chloro-3-nitrophenol are dissolved in 1,300 ml of dimethylformamide heated to 70° C. beforehand. 3 mols of powdered potassium hydroxide (210 g of 80% pure potassium hydroxide) are added to this solution and 3 mols (534 g) of glycol bromohydrin are then introduced in the course of 30 minutes, with stirring, whilst keeping the temperature at 70° C. When the addition has ended, the reaction medium is kept at 70° C. for 1 hour. 1 mol of powdered potassium hydroxide (70 g of 80% pure potassium hydroxide) and 1 mol of glycol bromohydrin (178 g) are then added. After heating for 1 hour, a further 1 mol of potassium hydroxide and 1 mol of glycol bromohydrin are added. The heating is continued for a further 1 hour and the cooled reaction medium is then poured into 7.5 liters of iced water. The expected product precipitates. It is filtered off and washed carefully with a 3N solution of sodium hydroxide and then with water. After drying in vacuo, it melts at 96° C.

2nd step: Preparation of 3-nitro-4-(β-aminoethyl)-aminophenoxyethanol.

0.4 mol (87 g) of 3-nitro-4-chlorophenoxyethanol in 225 ml of ethylenediamine are heated under reflux for 1 hour. The cooled reaction medium is poured into 500 g of iced water. The solution is rendered alkaline to pH 10 with a 10N solution of sodium hydroxide. The expected product crystallises. It is filtered off, washed with cold water and dried in vacuo at 50° C. It melts at 110° C. After recrystallisation from ethanol, it melts at 112°C.

| Analysis | Calculated for $C_{10}H_{15}N_3O_4$ | Found |
|---|---|---|
| C % | 49.78 | 49.86 |
| H % | 6.27 | 6.32 |
| N % | 17.42 | 17.35 |
| O % | 26.53 | 26.41 |

REFERENCE EXAMPLE 2

Preparation of 3-nitro-4-N-(β-hydroxyethyl)-aminophenyl β-hydroxypropyl ether.

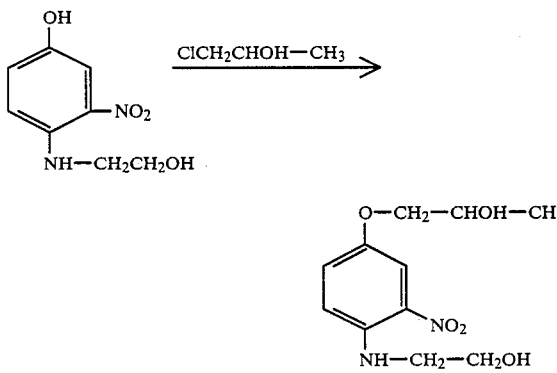

A solution of 0.2 mol (39.6 g) of 3-nitro-4-N-(β-hydroxyethyl)-aminophenol in 104 ml of a 2.3N solution of sodium hydroxide (0.24 mol) is heated beforehand to about 100° C. and 0.24 mol (22.7 g) of 1-chloropropan-2-ol is then added thereto. After the reaction medium has been kept in a boiling water-bath for 2 hours, it is and with 0.12 mol (11.34 g) of 1-chloropropan-2-ol. The heating is maintained for a further 2 hours in the boiling water-bath. After cooling to 0° C., the medium is rendered alkaline to pH 9 with a solution of sodium hydroxide. The expected product crystallises and it is filtered off and washed with a normal solution of sodium hydroxide and then with water. After drying in vacuo at 60° C., it melts at 118° C. After recrystallisation from ethanol and recrystallisation from ethyl acetate, it melts at 122° C.

| Analysis | Calculated for $C_{11}H_{16}N_2O_5$ | Found |
|---|---|---|
| C % | 51.56 | 51.73 |
| H % | 6.29 | 6.24 |
| N % | 10.93 | 10.82 |
| O % | 31.22 | 31.15 |

In the preceding examples, the tradenames used denote the following products:

Cemulsol NP4: Nonylphenol containing 4 mols of ethylene oxide, sold by Rhône Poulenc.
Cemulsol NP9: Nonylphenol containing 9 mols of ethylene oxide, sold by Rhône, Poulenc.
Cellosize WPO3: Hydroxyethylcellulose sold by Union Carbide.
Lauramide: Lauric acid monoethanolamide sold by Witco.
Alfol $C_{16/18}$: Cetyl/stearyl alcohol sold by Condea.
Lanette wax E: Partially sulphated cetyl/stearyl alcohol sold by Henkel.
Cemulsol B: Oxyethyleneated castor oil sold by Rhône Poulenc.
Carbopol 934: Acrylic acid polymer with a molecular weight of 2 to 3 million, sold by Goodrich Chem. Company.
Trilon B: Ethylenediaminetetraacetic acid.

We claim:

1. Process for the preparation of a nitroaniline which comprises reacting a compound of the formula $RNH_2$ with 3,4-methylenedioxynitrobenzene to produce a product of the formula:

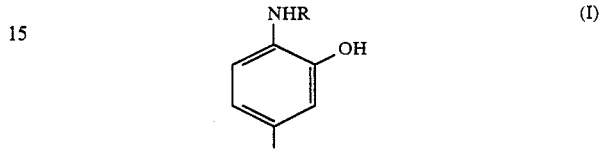 (I)

or a salt thereof, in which R denotes hydrogen, alkyl, monohydroxyalkyl or polyhydroxyalkyl, alkoxyalkyl, or aminoalkyl of the formula:

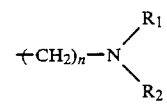

in which $R_1$ and $R_2$, which are identical or different, denote hydrogen, alkyl or monohydroxyalkyl or polyhydroxyalkyl and n denotes an integer from 2 to 4.

2. Process according to claim 1 in which 3,4-methylenedioxynitrobenzene is heated in an excess of amine of the formula $RNH_2$, at a temperature of 70° to 170° C., for 1 to 30 hours.

3. Process according to claim 1 in which R denotes alkyl, monohydroxyalkyl or polyhydroxyalkyl or alkoxyalkyl and a dilute solution of hydrochloric acid is added to the crude reaction product, the product insoluble in the hydrochloric acid medium is isolated, and, after washing with water, is treated with a dilute solution of sodium hydroxide, the resulting mixture is filtered and the product isolated after acidification of the filtrate.

4. Process according to claim 1 in which R denotes

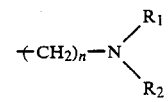

and the crude reaction product is taken up in a 2 to 3N solution of hydrochloric acid, the product crystallising in the form of the hydrochloride after cooling.

5. Process according to claim 1 in which an amine of the formula $R_1NH_2$, in which $R_1$ denotes $—CH_2CH_2OH$ or $—CH_2CHOHCH_3$, is reacted with 3,4-methylenedioxynitrobenzene using an excess of amine of the formula $R_1NH_2$, at a temperature of 70° to 170° C., for 1 to 30 hours, a dilute solution of hydrochloric acid is added to the crude reaction product obtained, the product insoluble in the hydrochloric acid medium is filtered off to give a compound of the formula:

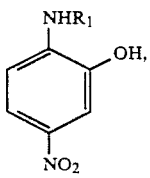

the mother liquors resulting from the filtration are rendered alkaline with a solution of sodium hydroxide so as to precipitate a product of the formula:

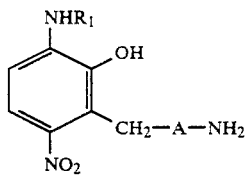

in which A denotes —OCH$_2$CH$_2$ or

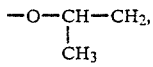

the product thus obtained being purified.

6. Process according to claim 1 in which R denotes methyl, ethyl, propyl, n-butyl, β-hydroxyethyl, β-aminoethyl or diethylaminoethyl.

7. A process for the preparation of nitroaniline which comprises heating 3,4-methylenedioxynitrobenzene with an excess of an amine of the formula RNH$_2$, at a temperature of 70° to 170° C., for 1 to 30 hours to produce a product of the formula:

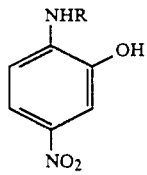

or a salt thereof, in which R denotes hydrogen, alkyl, monohydroxyalkyl or polyhydroxyalkyl, alkxoyalkyl, or aminoalkyl of the formula:

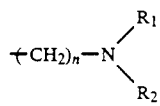

in which R$_1$ and R$_2$, which are identical or different, denote hydrogen, aklyl or monohydroxyalkyl or polyhydroxyalkyl and n denotes an integer from 2 to 4.

8. A process for the preparation of nitroaniline which comprises heating in the presence of only non-polar solvents, 3,4-methylenedioxynitrobenzene with an excess of an amine of the formula RNH$_2$, at a temperature of 70° to 170° C., for 1 to 30 hours to produce a product of the formula:

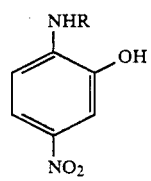

or a salt thereof, in which R denotes hydrogen, alkyl, monohydroxyalkyl or polyhydroxyalkyl, alkoxyalkyl, or aminoalkyl of the formula:

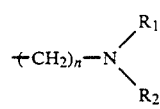

in which R$_1$ and R$_2$, which are identical or different, denote hydrogen, alkyl or monohydroxyalkyl or polyhydroxyalkyl and n denotes an integer from 2 to 4.

* * * * *